United States Patent [19]

Frewer et al.

[11] Patent Number: 4,631,915
[45] Date of Patent: Dec. 30, 1986

[54] GAS TURBINE AND STEAM POWER-GENERATING PLANT WITH INTEGRATED COAL GASIFICATION PLANT

[75] Inventors: Hans Frewer, Marloffstein; Rainer Müller, Erlangen; Ulrich Schiffers, Eckental, all of Fed. Rep. of Germany

[73] Assignee: Kraftwerk Union Aktiengesellschaft, Mülheim, Fed. Rep. of Germany

[21] Appl. No.: 725,012

[22] Filed: Apr. 18, 1985

[30] Foreign Application Priority Data

Apr. 21, 1984 [DE] Fed. Rep. of Germany ....... 3415224

[51] Int. Cl.$^4$ ............................................... F02C 3/28
[52] U.S. Cl. ................... 60/39.12; 60/39.182
[58] Field of Search ............... 60/39.02, 39.12, 39.182, 60/39.464

[56] References Cited

U.S. PATENT DOCUMENTS

| | | | |
|---|---|---|---|
| 3,533,739 | 10/1970 | Pelczarski et al. | ..................... 23/134 |
| 4,019,314 | 4/1977 | Springmann | ..................... 60/39.12 |
| 4,250,704 | 2/1981 | Bruckner et al. | ..................... 60/39.12 |

FOREIGN PATENT DOCUMENTS

| | | | |
|---|---|---|---|
| 2067668 | 7/1981 | United Kingdom | ............... 60/39.12 |
| 2075124 | 11/1981 | United Kingdom | ............... 60/39.12 |
| 2134601 | 8/1984 | United Kingdom | ............... 60/39.12 |

Primary Examiner—Louis J. Casaregola
Attorney, Agent, or Firm—Herbert L. Lerner; Laurence A. Greenberg

[57] ABSTRACT

Gas turbine and steam power generating station with an integrated coal gasification plant which is supplied with oxygen via an air decomposition plant, with a methanol synthesis plant connected to the coal gasification plant, with a steam generating station part connected to the exhaust heat boiler of the gas turbine, as well as with a nitrogen line leading from an air decomposition plant to the combustion chamber of the gas turbine. The coal gasifier for the hydrogenating coal gasification is connected to a hydrogen supply line; the coal gasifier is followed, for utilizing the residual coke, by an iron bath gasifier, which is followed on the exhaust gas side by a converting plant and a carbon dioxide scrubbing plant connected to the hydrogen supply line. The exhaust gas line of the coal gasifier is connected via a gas purifier to a methanol synthesis plant and the exhaust gas line of the methanol synthesis plant is connected to the combustion chamber of the gas turbine.

10 Claims, 1 Drawing Figure

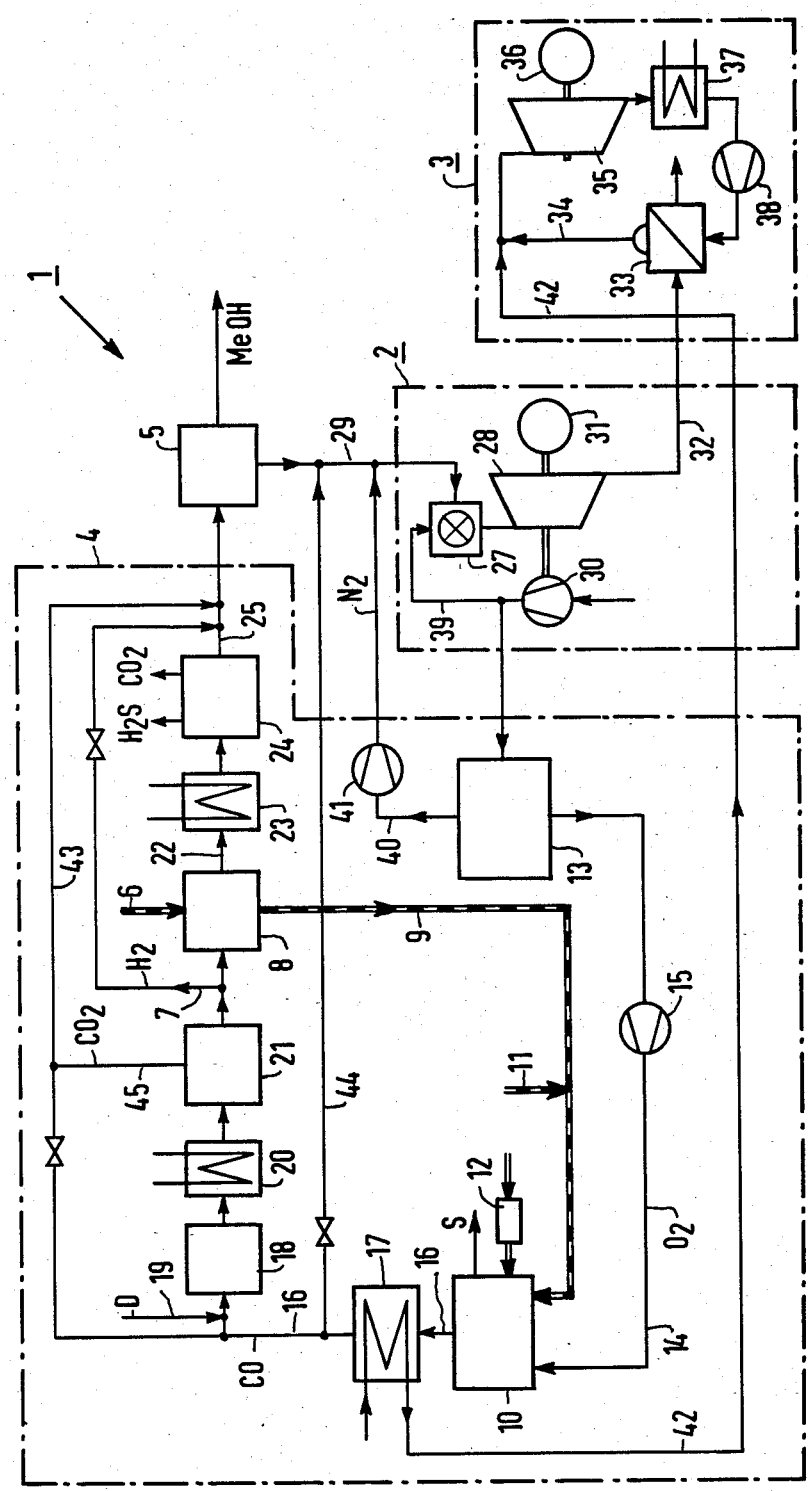

GAS TURBINE AND STEAM POWER-GENERATING PLANT WITH INTEGRATED COAL GASIFICATION PLANT

BACKGROUND OF THE INVENTION

1. Field of the Invention

The invention relates to a gas-turbine and steam power-generating plant with a coal gasification plant which is supplied with oxygen via an air separation plant with a methanol synthesis plant connected to the coal gasification plant, with a part of the steam power-generating plant connected to a waste heat boiler of the gas turbine, as well as with a nitrogen line leading from the air separation plant to the combustion chamber of the gas turbine.

2. Description of the Prior Art

A gas turbine and steam generating plant with a coal gasification plant and with a methanol synthesis plant has been proposed (German Application No. P 33 19 732.6 and U.S. application Ser. No. 614,470 filed May 25, 1984). It is characterized by extraordinary flexibility in the generation of electric power. Because the generation of methanol is increased in times of low load, the coal gasifier can be operated in this gas-turbine and steam power generating plant always with constant power matched to its optimum efficiency. For this proposed power-generating concept, a hydrogen sulfide absorber and a Claus plant are necessary for removing the sulfur.

SUMMARY OF THE INVENTION

An object of the invention is to provide a new and improved power-generating station in which power can be manufactured more cheaply and in which the exhaust gases are free of sulfur and suitable for conversion into methanol.

With the foregoing and other objects in view, there is provided in accordance with the invention a gas-turbine and steam power-generating station comprising an integrated coal gasification plant, an air separation plant which supplies oxygen therefrom to the integrated coal gasification plant, a methanol synthesis plant connected to the coal gasification plant, a steam generating station part connected to an exhaust heat boiler of the gas turbine, and a nitrogen line leading from an air separation plant to the combustion chamber of the gas turbine; the combination therewith of a coal gasifier to which a hydrogen supply line is connected for hydrogenating coal gasification to partially convert coal feed into a gas containing hydrogen, methane and carbon monoxide leaving residual coke, and an iron bath gasifier into which the residual coke is fed, for oxidizing the residual coke with said oxygen from the air separation plant to produce a gas containing carbon monoxide and to remove sulfur contained in the residual coke, a converting plant in which at least part of said gas containing carbon monoxide is reacted with steam to convert the carbon monoxide to hydrogen and carbon dioxide, a carbon dioxide scrubbing plant to remove said carbon dioxide leaving a gas containing principally hydrogen which goes to the hydrogen supply line, an exhaust gas line from the coal connected via a gas purifier to said methanol synthesis plant, and an exhaust gas line of the methanol synthesis plant connected to the combustion chamber of the gas turbine.

Other features which are considered as characteristic for the invention are set forth in the appended claims.

Although the invention is illustrated and described herein as embodied in a gas turbine and steam power-generating plant with integrated coal gasification plant, it is nevertheless not intended to be limited to the details shown, since various modifications may be made therein without departing from the spirit of the invention and within the scope and range of equivalents of the claims.

BRIEF DESCRIPTION OF THE DRAWING

The invention, however, together with additional objects and advantages thereof will be best understood from the following description when read in connection with the accompanying drawing which diagrammatically illustrates a gas-turbine steam power-generating station composed of a gas-turbine power-generating part, a steam-turbine power-generating part, a plant for the coal gasification, and a plant for making chemical raw material (methanol synthesis plant).

DESCRIPTION OF THE PREFERRED EMBODIMENT

The invention relates to a gas-turbine and steam power-generating station with an integrated coal gasification plant supplied with oxygen via an air separation plant and a methanol synthesis plant connected to the coal gasification plant, with a steam power-generating plant connected to the waste heat boiler of the gas turbine, as well as with a nitrogen line leading from an air decomposition plant to the combustion chamber of the gas turbine. In such a power generating station, the problem arises to employ the residual coke with high sulfur content produced in the coal gasification as usefully as possible without exceeding the emission limit for sulfur dioxide and, at the same time, to minimize the investment for such a power-generating station. For this purpose, the invention provides that the coal gasifier for the hydrogenating coal gasification is connected to a hydrogen supply line; the coal gasifier is followed by an iron bath gasifier for utilizing the residual coke and the iron bath gasifier is followed on the exhaust gas side by a converting plant and a carbon dioxide scrubbing plant and the exhaust gas line of the coal gasifier is connected via a gas purifier to a methanol synthesis plant and the exhaust gas line of the methanol synthesis plant is connected to the combustion chamber of the gas turbine. A power generating station according to the invention is suitable for using fossil fuels of all kinds.

By virtue of the hydrogenating coal gasification and the subsequent gasification of the sulfur-containing residual coke in an iron bath gasifier, the entire sulfur contained in the fossil fuel is bound into the slag floating on the iron bath, without the aid of further building blocks, by the mere addition of lime. The slag is then drained off from time to time. At the same time, methane is generated in considerable quantities and also higher-molecular weight hydrocarbons in smaller quantities are generated by the hydrogenating coal gasification.

The iron bath gasifier, in addition to binding the sulfur, also fulfills the task of making available in sufficient quantities carbon monoxide gas required for the generation of hydrogen. Carbon monoxide is then converted, in the conversion plant connected to the gas side, into hydrogen gas and carbon dioxide gas. The carbon dioxide gas can be scrubbed in the connected carbon dioxide scrubbing plant. Since, however, a mass ratio of carbon monoxide to hydrogen of 1:2 is required for the methanol synthesis, the conversion plant and the carbon dioxide scrubbing plant need to be designed only for part of the total quantity of exhaust gas of the iron bath gasifier. This leads to a reduction in size of the conversion plant and the carbon dioxide scrubbing plant. Because, in the methanol synthesis, carbon dioxide is also converted into methanol with hydrogen, the carbon dioxide washed out in the carbon dioxide scrubbing plant is admixed to the carbon monoxide gas flowing into the methanol synthesis plant. In this manner, the requirement for carbon monoxide can be reduced, so that larger quantities become available for the generation of hydrogen. With this power plant concept, the recirculation of the hydrogen gas, otherwise required, into the hydrogenating coal gasifier with the low-temperature gas composition plant, the reheating of the hydrogen gas and the compressor for the hydrogen gas can be eliminated.

Due to the use of a continuous-flow methanol synthesis plant instead of a plant with recirculation of synthesis gas, the exact maintenance of the stoichiometric ratio of carbon monoxide gas and hydrogen gas is not necessary. Thereby, the otherwise required measuring and control devices can be simplified or made less expensive. Also, the compressor for the recirculating synthesis gas is no longer required and the carbon monoxide gas need not be converted to the otherwise required degree. In addition, greater flexibility in operation, particularly with respect to the utilization of the raw materials in the coal and iron bath gasifier and the type of fossil fuels used is achieved.

The hot exhaust gases of the iron bath gasifier are cooled down in a high-pressure steam generator and superheater immediately following th former. The high-pressure steam generated in the process can be fed directly to a steam turbine. Since it has the same pressure and temperature level as the steam generated in the waste heat boiler of the gas turbine, it can also be admixed to the latter.

Further flexibility in the operation of this power-generating station is achieved by the provision that part of the exhaust gases of the iron bath gasifier, leaving the high pressure steam generator, can be fed to the combustion chamber of the gas turbine via a separate line, together with the not reacted synthesis gases to the continuous-flow methanol synthesis plant. As a result, more fuel can be fed to the gas turbine for short times during peak load times and at the same time, the steam consumption for the smaller quantity of gas-containing carbon monoxide fed into the conversion plant can be reduced. Finally, the emission of nitric oxides can further be lowered in this power-generating station by the provision that the nitrogen separated from the oxygen in the air decomposition plant following the iron bath gasifier is fed to the burner of the gas turbine in a power-related manner in matched quantities. Thereby, the flame temperature can be kept below the temperature level required for nitric acid formation.

Further details of the invention will be explained with the aid of an embodiment example shown in the drawing, where a schematic presentation of a gas turbine steam power-generating station according to the invention is shown.

As shown in the drawing, the gas-turbine and steam power-generating station 1 according to the invention includes a gas-turbine power-generating part 2, a steam-turbine power-generating station part 3 and a plant 4, preceding the gas turbine power-generating station part, for the coal gasification, with a connected plant 5 for making chemical raw materials, which is a continuous-flow methanol synthesis plant in the embodiment example. The fossil fuels to be gasified (coal in the embodiment example) are transported via a coal line 6 to a coal gasifier 8 to which hydrogen is fed via a hydrogen supply line 7. The residual coke not reacted in the coal gasifier 8 is conducted via a coke line 9 to an iron bath gasifier 10. Additional fossil fuels can be fed through another coal line 11 which leads into the coke line 9. In addition, the iron bath gasifier 10 is provided with a dosing device 12 for feeding-in lime. The iron bath gasifier 10 is connected to an oxygen line 14 connected to an air separation plant 13. A compressor 15 is inserted into line 14 to overcome the pressure difference between plant 13 and gasifier 10.

In the iron bath gasifier 10, the fuel entering through line 9 is reacted with oxygen from line 14 to produce a predominantly carbon monoxide-containing gas. A heat exchanger plant 17 with a high-pressure steam generator is connected to the exhaust gas line 16 of the iron bath gasifier 10. A medium-pressure steam line 19, designated D, leads into the exhaust gas line 16 of the iron bath gasifier 10, leaving the heat exchanger plant, before it is connected to a conversion plant 18. This conversion plant 18, in which the carbon monoxide gas is reacted with the admixed steam to produce hydrogen and carbon dioxide, is connected on the discharge side to a further heat exchanger 20 as well as following the same, to a carbon dioxide scrubbing plant 21, in which the carbon dioxide is washed out. The gas leaving the carbon dioxide scrubbing plant which contains principally hydrogen, is fed into the hydrogen supply line 7. This hydrogen supply line 7 is connected to, among other things, the hydrogenating coal gasifier 8, in which the fossil fuel is used and reacted into a gas rich in methane.

The exhaust gas line 22 of the hydrogenating coal gasifier 8 is connected via a heat exchanger plant 23 to a gas purifier 24 consisting of a dust-remover plant and a carbon dioxide and hydrogen sulfide scrubbing plant. The synthesis gas line 25 is connected to a continuous-flow methanol synthesis plant 5. The hydrogen supply line 7 also leads into the synthesis gas line 25. The continuous-flow methanol synthesis plant on its exhaust gas side is connected to a fuel line 29 leading to the combustion chamber 27 of the gas turbine 28.

The gas turbine 28 of the gas turbine part 2 of the power generating station drives an air compressor 30 for the combustion air as well as a generator 31. A waste heat boiler 33 is connected to the exhaust gas line 32 of the gas turbine 28. The steam turbine 35 of the steam turbine power generating station part 3 is connected to the high-pressure steam line 34 of the waste heat boiler 33. Steam turbine 35 is coupled to a generator 36. The steam exit side of the steam turbine 35 is followed by a condenser 37, a condensate pump (not shown), a feedwater tank (not shown) and at least one feedwater pump 38 connected to the waste heat boiler 33.

The compressed-air line 39 of the air compressor 30 is connected to the combustion chamber 27 of the gas turbine 28 and to the air separation plant 13. The oxygen line 14 of the air separation plant 13 is connected via the compressor 15 to the iron bath gasifier 10 and the nitrogen line 40 of the air separation plant 13 is connected via a further compressor 41 to the fuel line 29 leading to the combustion chamber 27. The high-pressure steam line 42 of the heat exchanger plant 17 following the iron bath gasifier 10 on the gas side opens into the high-pressure steam line 34 leading from the waste-heat boiler 33 to the steam turbine 35. The hydrogen supply line 7, and in addition a second exhaust gas line 43 for the carbon monoxide-containing exhaust gas of the iron bath gasifier which is branched off behind the heat exchanger plant 17 following the iron bath gasifier 10 open into the synthesis gas line 25 leading to the continuous-flow methanol synthesis plant 5. A third exhaust gas line 44 branches off from exhaust gas line 16 and leads directly into the fuel line 29 which latter leads directly into the combustion chamber 27 of the gas turbine. The exhaust gas line 45 for the carbon dioxide separated in the carbon dioxide scrubbing plant 21 is connected to the exhaust gas line 43 for the carbon monoxide-containing exhaust gas leading to the methanol synthesis plant 5.

The fossil fuels charged into the coal gasifier 8 are gasified by means of the hydrogen gas taken from the hydrogen supply line 7, are gasified to a gas containing substantial proportions of hydrogen and methane and some carbon monoxide. The remaining residual coke is fed into the iron bath gasifier 10 via the coke line 9, optionally while admixing further fossil fuels, and are gasified there by means of the oxygen taken from the air separation plant, to a gas which contains substantially carbon monoxide. For binding the sulfur contained in the residual coke and in the optionally introduced fossil fuels, lime is added into the iron bath gasifier via a separate dosing device 12. In the slag thus formed on the iron bath, the entire sulfur contained in the fuel introduced in the iron bath gasifier can be bound and discharged from time to time. The iron bath gasifier, due to feeding in high B.T.U. residual coke with low B.T.U. fuel such as lignite, oil shale, heavy oil residues, oil sand, etc. and their mixtures can be operated with an exothermic heat balance adequate for good operation.

The very hot exhaust gas leaving the iron bath gasifier 10 which contains principally carbon monoxide gas is cooled down in a heat exchanger plant 17 and is conducted via the exhaust gas line 16 into a converting plant 18. Before it opens into the converting plant, steam is fed via a medium-pressure steam line 19, to this carbon monoxide-containing gas, so that the carbon monoxide gas together with the steam can be reacted with the steam in the converting plant to form hydrogen and carbon monoxide. The gas leaving the converting plant 18 is fed, after being cooled in a heat exchanger into a carbon dioxide scrubbing plant 21, in which it is freed of the carbon dioxide. The gas leaving the carbon dioxide scrubbing plant, which now contains mostly hydrogen with minor amounts of other gases, is now fed into the hydrogen supply line 7.

The exhaust gas leaving the coal gasifier 8 which now contains principally methane and hydrogen is cooled in the heat exchanger plant 23 and is purified in the gas purifier 24 of suspended ash particles as well as of hydrogen sulfide and residual carbon dioxide. It is then fed, via the synthesis gas line 25, to the continuous-flow methanol synthesis plant. The hydrogen supply line 7 as well as a second exhaust gas line 43 for the unconverted, carbon monoxide-containing exhaust gas of the iron bath gasifier is connected to the synthesis gas line. According to the ratio of the share of carbon monoxide-containing exhaust gas of the iron bath gasifier, which is conducted through this second exhaust gas line 43 and through the conversion plant 18, the stoichiometric ratio for the following continuous-flow methanol synthesis plant of hydrogen to carbon monoxide can be set as 2:1. The synthesis exhaust gas leaving the continuous-flow synthesis plant which is not reacted to methanol and in which the methane passing through the gas purifier is contained, is transported via the fuel line into the combustion chamber 27 of the gas-turbine generating station part.

Because the unreacted residual synthesis gases are burned in the combustion, a plant for removing the methane from the exhaust gas of the hydrogenating coal gasifier can be omitted and the requirements as to maintaining the stoichiometric ratio of carbon monoxide and hydrogen gas in the synthesis gas are greatly reduced. In addition, setting it by regulating the gas flow in the second exhaust gas line 43 of the iron bath gasifier 10 is simple.

This concept of the gas-turbine steam power-generating plant 1 also permits unconverted, carbon monoxide-containing exhaust gas of the iron bath gasifier to be introduced via the third exhaust gas line 44 directly into the fuel line 29 leading to the combustion chamber 27 of the gas turbine 28 also in a starting-up phase and in the event of sudden load changes. Thereby, the power output of the gas turbine can be changed in a short term, and also the amount of steam generated in the exhaust-heat boiler for the steam turbine 35 can be increased. At the same time, due to the decrease of the quantity of exhaust gas to be converted, less medium-pressure steam need be branched off for conversion. This increases the flexibility of the power-generating station in matching its electric power output to the requirements of the network, without the need to appreciably change the output of the hydrogenating coal gasifier or the iron bath gasifier.

By additionally feeding nitrogen into the fuel line 29 of a combustion chamber 27, the flame temperature, in addition, can be lowered so far that the nitric oxide emission can be minimized for a given output.

The foregoing is a description corresponding, in substance, to German application No. P 34 15 224.5, dated Apr. 21, 1984, international priority of which is being claimed for the instant application and which is hereby made part of this application.

Any material discrepancies between the foregoing specification and the specification of the aforementioned corresponding German application are to be resolved in favor of the latter.

There is claimed:

1. A gas turbine and steam power-generating plant with an integrated coal gasification plant and with a methanol synthesis plant, comprising a hydrogenating coal gasifier for partially converting coal containing sulfur in the presence of hydrogen into a gas containing principally hydrogen and methane and lesser amounts of carbon monoxide and hydrogen sulfide leaving residual coke containing sulfur, coal feed means for feeding coal containing sulfur into the hydrogenating coal gasifier, a hydrogen supply line connected to the hydrogenating coal gasifier for feeding hydrogen thereto, an exhaust gas line from the hydrogenating coal gasifier connected to a gas purifier for removal of hydrogen sulfide, connecting means for the transfer of purified gas containing principally hydrogen and methane from the gas purifier to a methanol synthesis plant for converting hydrogen and carbon monoxide into methanol, a coke line for conducting the residual coke from the hydrogenating coal gasifier to an iron bath gasifier having a molten iron body with slag floating thereon wherein the residual coke is oxidized with oxygen fed to the iron bath gasifier to produce a gas containing carbon monoxide and the sulfur contained in the residual coke is bound into the slag, a dosing device for feeding-in lime into the iron bath gasifier to aid in binding the sulfur in the slag, a slag outlet for the discharge of slag containing sulfur from the iron bath gasifier, an air separation plant into which air is fed and separated into an oxygen fraction and a nitrogen fraction, an oxygen line from the air separation plant to supply the oxygen fed to the iron bath gasifier to oxidize the residual coke therein to produce a gas containing carbon monoxide, a first exhaust gas line for conducting a portion of the gas containing carbon monoxide from the iron bath gasifier into a converting plant in which at least part of the gas containing carbon monoxide is reacted with steam to convert the carbon monoxide to hydrogen and carbon dioxide, a steam line leading into the converting plant for supplying the steam for reaction with carbon monoxide, a discharge line for conducting the exhaust gas containing hydrogen and carbon dioxide from the converting plant to a carbon dioxide scrubbing plant to remove said carbon dioxide leaving a gas containing principally hydrogen which goes to the hydrogen supply line, a second exhaust gas line for conducting another portion of the gas containing carbon monoxide from the iron bath gasifier into the methanol synthesis plant for reaction with hydrogen therein to produce methanol, a gas turbine with a combustion chamber coupled with an electric generator for generating electricity, an exhaust gas line of the methanol synthesis plant connected to the combustion chamber of the gas turbine to supply fuel for combustion in the combustion chamber, a compressor with a connecting air line for feeding combustion air to the combustion chamber, a nitrogen line leading from the air separation plant to feed nitrogen into the combustion chamber of the gas turbine to minimize nitrogen oxide emission, a steam power generating plant having a waste heat boiler for generating steam connected to an exhaust line from the gas turbine, a steam turbine connected to the waste heat boiler to receive steam to drive the steam turbine, a generator coupled with the steam turbine to generate electricity, and a condenser, pump and tank for recirculating steam condensate from the steam turbine to the waste heat boiler.

2. Gas-turbine and steam power-generating plant according to claim 1, including means for feeding additional fossil fuel to the iron bath gasifier.

3. Gas turbine and steam power generating plant according to claim 1, wherein the exhaust gas line of the iron bath gasifier is conducted through a heat exchanger plant with a steam generator connected on the steam side to the steam turbine of the steam power-generating plant part.

4. Gas turbine and steam power generating plant according to claim 1, wherein the hydrogen supply line is connected, in addition to the coal gasifier, also to the methanol synthesis plant.

5. Gas turbine and steam power generating plant according to claim 3, including a second exhaust gas line for conducting part of the exhaust gas of the iron bath gasifier leaving the heat exchanger plant directly to the methanol synthesis plant.

6. Gas turbine and steam power generating plant according to claim 1, wherein said steam line leading into the converting plant is a medium-pressure steam line which opens into the first exhaust gas line from the iron bath gasifier leading into the converting plant.

7. Gas turbine and steam power generating plant according to claim 3, including a third exhaust gas line for conducting part of the exhaust gas of the iron bath gasifier leaving the heat exchanger plant directly into a fuel line leading to the combustion chamber of the gas turbine.

8. Gas turbine and steam power generating plant according to claim 1, wherein the methanol synthesis plant is a plant for the continuous flow methanol synthesis.

9. Gas turbine and steam power generating plant according to claim 1, including a separate line for feeding the carbon dioxide separated in the carbon dioxide scrubbing plant into the methanol synthesis plant.

10. Gas turbine and steam power generating plant according to claim 2, wherein the additional fossil fuel fed to the iron bath gasifier is a low B.T.U. fuel selected from the group consisting of lignite, oil shale, heavy oil residues, oil sand and mixtures thereof, for operating the iron bath gasifier with sufficient exothermic heat balance.

* * * * *